United States Patent
Campeau et al.

(10) Patent No.: US 8,674,093 B2
(45) Date of Patent: Mar. 18, 2014

(54) PROCESS FOR THE PREPARATION OF AN OREXIN RECEPTOR ANTAGONIST

(75) Inventors: Louis-Charles Campeau, Vaudreuil-Dorian (CA); John Y. Chung, Edison, NJ (US); Danny Gauvreau, Saint-Lazare (CA); Melina Girardin-Rondeau, Jonquiere (CA); Gregory Hughes, Scotch Plains, NJ (US); Kevin M. Maloney, Piscataway, NJ (US); Christophe Mellon, Saint-Redempteur (CA); Jeffrey C. Moore, Westfield, NJ (US); Paul O'Shea, Westmount (CA); Stephane Ouellet, Saint Lazare (CA)

(73) Assignees: Merck Canada Inc., Kirkland, Quebec (CA); Merck Sharp & Dohme Corp., Rahway, NJ (US)

( * ) Notice: Subject to any disclaimer, the term of this patent is extended or adjusted under 35 U.S.C. 154(b) by 319 days.

(21) Appl. No.: 12/993,341

(22) PCT Filed: May 18, 2009

(86) PCT No.: PCT/US2009/044284
§ 371 (c)(1),
(2), (4) Date: Jan. 26, 2011

(87) PCT Pub. No.: WO2009/143033
PCT Pub. Date: Nov. 26, 2009

(65) Prior Publication Data
US 2011/0165632 A1    Jul. 7, 2011

Related U.S. Application Data

(60) Provisional application No. 61/128,505, filed on May 22, 2008.

(51) Int. Cl.
C07D 401/12    (2006.01)
C07D 401/14    (2006.01)
C07D 403/14    (2006.01)
C07D 239/24    (2006.01)

(52) U.S. Cl.
USPC .......................... 544/242; 546/184; 546/193

(58) Field of Classification Search
USPC .................................... 544/242; 546/184, 193
See application file for complete search history.

(56) References Cited

U.S. PATENT DOCUMENTS

2010/0168134 A1    7/2010    Breslin et al.

FOREIGN PATENT DOCUMENTS

WO    2006117669    11/2006
WO    2008147518    12/2008

*Primary Examiner* — Venkataraman Balasubramanian
(74) *Attorney, Agent, or Firm* — J. Eric Thies; John C. Todaro

(57) ABSTRACT

The present invention is directed to processes for preparing a pyridyl piperidine compound which is an antagonist of orexin receptors, and which is useful in the treatment or prevention of neurological and psychiatric disorders and diseases in which orexin receptors are involved.

10 Claims, No Drawings

PROCESS FOR THE PREPARATION OF AN OREXIN RECEPTOR ANTAGONIST

CROSS REFERENCE TO RELATED APPLICATIONS

This application is a U.S. National Phase application under 35 U.S.C. §371 of PCT Application No. PCT/US2009/44284, filed May 18, 2009, which claims priority under 35 U.S.C. §119(e) from U.S. Ser. No. 61/128,505, filed May 22, 2010.

BACKGROUND OF THE INVENTION

The orexins (hypocretins) comprise two neuropeptides produced in the hypothalamus: the orexin A (OX-A) (a 33 amino acid peptide) and the orexin B (OX-B) (a 28 amino acid peptide) (Sakurai T. et al., Cell, 1998, 92, 573-585). Orexins are found to stimulate food consumption in rats suggesting a physiological role for these peptides as mediators in the central feedback mechanism that regulates feeding behaviour (Sakurai T. et al., Cell, 1998, 92, 573-585). Orexins regulate states of sleep and wakefulness opening potentially novel therapeutic approaches for narcoleptic or insomniac patients (Chemelli R. M. et al., Cell, 1999, 98, 437-451). Orexins have also been indicated as playing a role in arousal, reward, learning and memory (Harris, et al., Trends Neurosci., 2006, 29 (10), 571-577). Two orexin receptors have been cloned and characterized in mammals. They belong to the super family of G-protein coupled receptors (Sakurai T. et al., Cell, 1998, 92, 573-585): the orexin-1 receptor (OX or OX1R) is selective for OX-A and the orexin-2 receptor (OX2 or OX2R) is capable to bind OX-A as well as OX-B. The physiological actions in which orexins are presumed to participate are thought to be expressed via one or both of OX 1 receptor and OX 2 receptor as the two subtypes of orexin receptors.

Orexin receptors are found in the mammalian brain and may have numerous implications in pathologies such as depression; anxiety; addictions; obsessive compulsive disorder; affective neurosis; depressive neurosis; anxiety neurosis; dysthymic disorder; behaviour disorder; mood disorder; sexual dysfunction; psychosexual dysfunction; sex disorder; schizophrenia; manic depression; delirium; dementia; severe mental retardation and dyskinesias such as Huntington's disease and Tourette syndrome; eating disorders such as anorexia, bulimia, cachexia, and obesity; addictive feeding behaviors; binge/purge feeding behaviors; cardiovascular diseases; diabetes; appetite/taste disorders; emesis, vomiting, nausea; asthma; cancer; Parkinson's disease; Cushing's syndrome/disease; basophile adenoma; prolactinoma; hyperprolactinemia; hypophysis tumour/adenoma; hypothalamic diseases; inflammatory bowel disease; gastric diskinesia; gastric ulcers; Froehlich's syndrome; adrenohypophysis disease; hypophysis disease; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth deficiency; dwarfism; gigantism; acromegaly; disturbed biological and circadian rhythms; sleep disturbances associated with diseases such as neurological disorders, neuropathic pain and restless leg syndrome; heart and lung diseases, acute and congestive heart failure; hypotension; hypertension; urinary retention; osteoporosis; angina pectoris; myocardinal infarction; ischemic or haemorrhagic stroke; subarachnoid haemorrhage; ulcers; allergies; benign prostatic hypertrophy; chronic renal failure; renal disease; impaired glucose tolerance; migraine; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; emesis, nausea, vomiting; conditions associated with visceral pain such as irritable bowel syndrome, and angina; migraine; urinary bladder incontinence e.g. urge incontinence; tolerance to narcotics or withdrawal from narcotics; sleep disorders; sleep apnea; narcolepsy; insomnia; parasomnia; jet lag syndrome; and neurodegenerative disorders including nosological entities such as disinhibition-dementia-parkinsonism-amyotrophy complex; pallido-ponto-nigral degeneration; epilepsy; seizure disorders and other diseases related to general orexin system dysfunction.

SUMMARY OF THE INVENTION

The present invention is directed to processes for preparing a pyridyl piperidine compound which is an antagonist of orexin receptors, and which is useful in the treatment or prevention of neurological and psychiatric disorders and diseases in which orexin receptors are involved.

DETAILED DESCRIPTION OF THE INVENTION

The present invention is directed to a process for preparing a compound of the formula I:

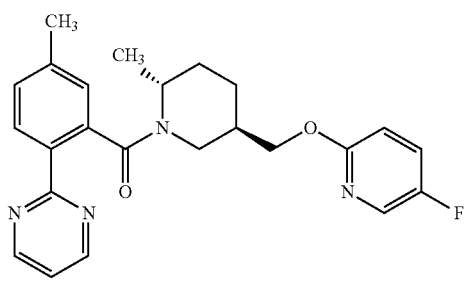

or a pharmaceutically acceptable salt thereof, which comprises:

contacting a compound of the formula II:

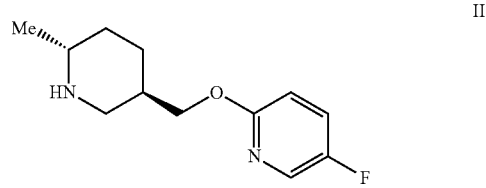 [SMILES: C[C@@H]1CC[C@@H](COc2ccc(F)cn2)CN1]

with a compound of the formula III:

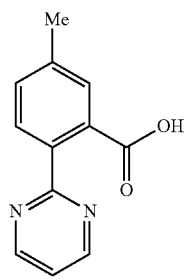

in the presence of a coupling agent,
to give the compound of the formula I.

In a specific embodiment, the present invention is directed to a process for preparing a compound of the formula I:

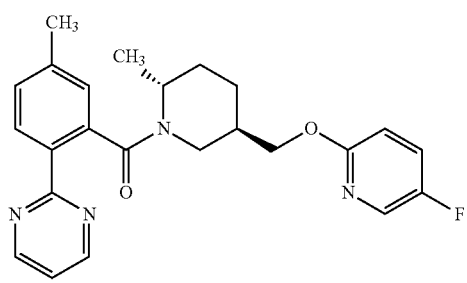

or a pharmaceutically acceptable salt thereof,
which comprises:
contacting a compound of the formula H:

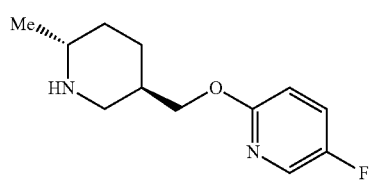

with a compound of the formula III:

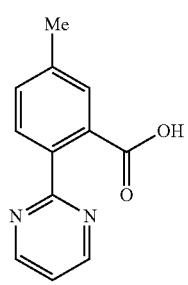

in the presence of 1-propyl phosphonic anhydride and a weak organic base to give the compound of the formula I.

The present invention is further directed to a process for preparing a compound of the formula I:

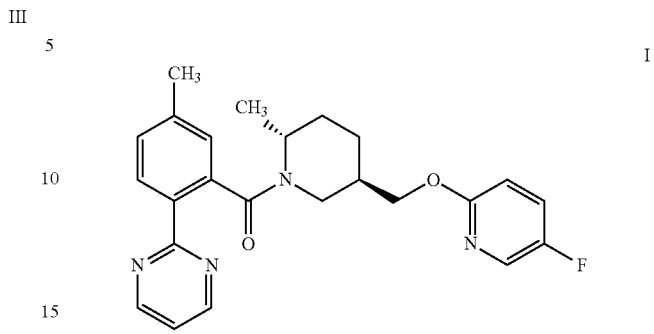

or a pharmaceutically acceptable salt thereof,
which comprises:
contacting a compound of the formula V:

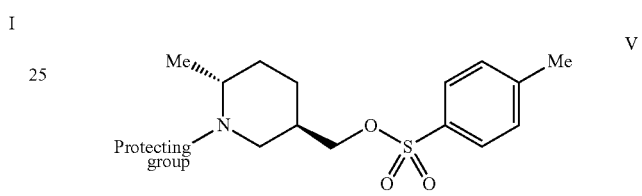

with 5-fluoro-2-hydroxypyridine of the formula VI:

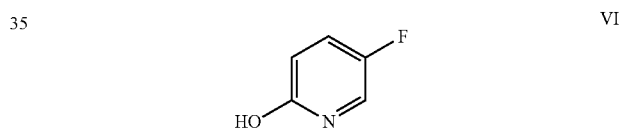

in the presence of cesium carbonate to give the compound of the formula IV:

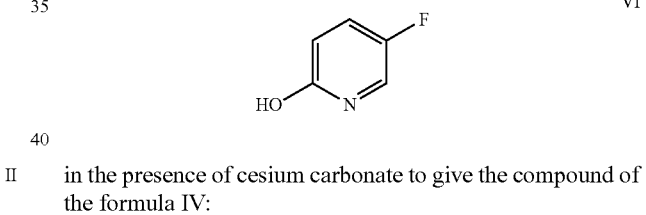

followed by removal of the protecting group in the compound of the formula IV to give the compound of the formula II:

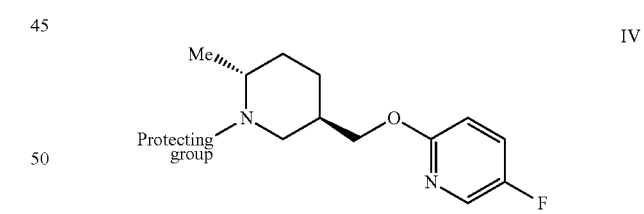

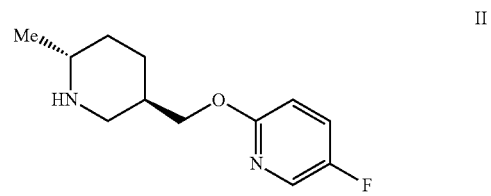 [SMILES: C[C@@H]1CC[C@@H](COc2ccc(F)cn2)CN1]

followed by contacting the compound of the formula II with a compound of the formula III:

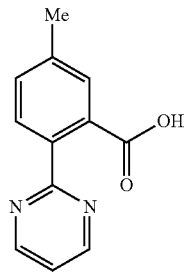

in the presence of a coupling agent,
to give the compound of the formula I.

In an embodiment of the present invention, the step of contacting a compound of formula V with a compound of formula VI to give a compound of formula IV is conducted in an amide solvent. An amide solvent is an organic solvent containing an amide functionality.

In an embodiment of the present invention, the amide solvent is selected from the group consisting of: formamide, N-methylformamide, N,N-dimethylformamide, acetamide, N-methylacetate, N,N-dimethylacetamide, N,N,N',N'-tetramethylurea, 2-pyrrolidone, and N-methylpyrrolidone.

In an embodiment of the present invention, the amide solvent is N,N-dimethylformamide or N-methylpyrrolidone.

In an alternate embodiment, the present invention is directed to a process for preparing a compound of the formula I:

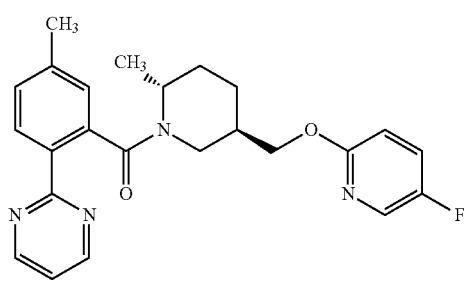

or a pharmaceutically acceptable salt thereof,
which comprises:
contacting a camphorsulfonate salt of the formula VII:

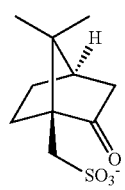 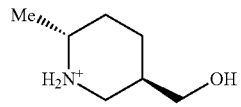

with 2,5-difluoropyridine of the formula VIa:

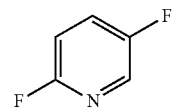

in the presence of a strong organic base to give the compound of the formula II:

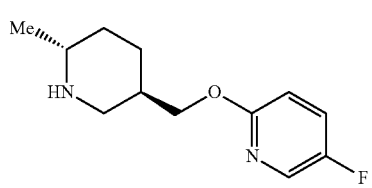

followed by contacting the compound of the formula II with a compound of the formula III:

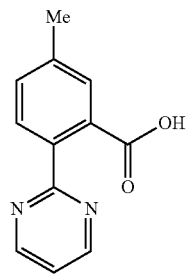

in the presence of a coupling agent,
to give the compound of the formula I.

In an embodiment of the present invention, the step of contacting camphorsulfonate salt of the formula VII with 2,5-difluoropyridine of the formula VIa, the strong organic base is selected from the group consisting of: sodium t-butoxide and sodium ethoxide. In an embodiment of the present invention, the strong organic base is sodium t-butoxide.

In an alternate embodiment, the present invention is directed to a process for preparing a compound of the formula V:

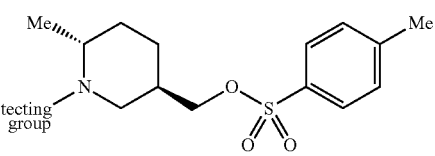

which comprises:
contacting methyl vinyl ketone of the formula XIII:

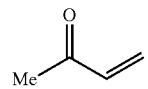

with dimethyl malonate of the formula XII:

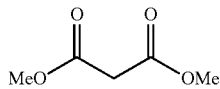

XII in the presence of a weak inorganic base to give a compound of the formula XI:

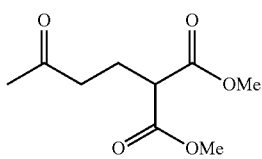

XI followed by biocatalytic transamination to give a compound of the formula X:

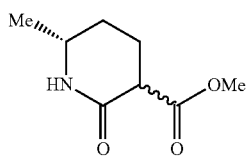

X followed by reduction with a first hydride reducing agent of the compound of the formula X to give a compound of the formula IX:

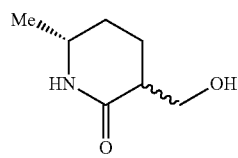

IX followed by reduction with a second hydride reducing agent of the compound of the formula IX to give a compound of the formula VIII:

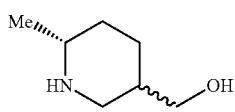

VIII followed by formation of the camphorsulfonate salt of the compound of the formula VIII and isolation to give a camphorsulfonate salt of the formula VII:

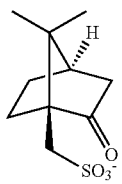 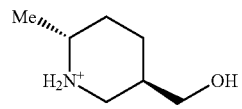

VII followed by protecting the free amine in the compound of the formula VII with an amino protecting group to give a compound of the formula VI:

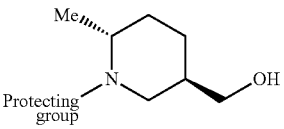

VI followed by contacting the compound of formula VI with tosyl chloride in the presence of a weak organic base to give the compound of the formula V.

In an alternate embodiment, the compound of the formula X:

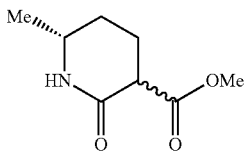

X may be reduced directly with a second hydride reducing agent to give the compound of the formula VIII:

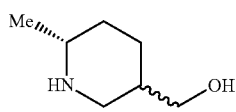

VIII

In an embodiment of the present invention, the step of contacting methyl vinyl ketone of the formula XIII with dimethyl malonate of the formula XII, the weak inorganic base is selected from the group consisting of: potassium carbonate, sodium carbonate and sodium bicarbonate. In an embodiment of the present invention, the weak inorganic base is potassium carbonate.

In an embodiment of the present invention, the biocatalytic transamination to give a compound of the formula X is conducted with a transaminase enzyme. In one embodiment, the transaminase enzyme is ATA-117 (commercially available from Codexis). In another embodiment, the transaminase enzyme Vibrio (commercially available from Codexis) may be used to provide the other enantiomer of the compounds of the formula X. In an embodiment of the present invention, the biocatalytic transamination with a transaminase enzyme is optionally conducted under conditions that remove the byproduct from the reaction of the transaminase enzyme. In an embodiment of the present invention, the biocatalytic transamination with a transaminase enzyme is optionally conducted in the presence of lactate dehydrogenase and glucose dehydrogenase to remove the byproduct from the reaction of the transaminase enzyme.

In an embodiment of the present invention, the reduction with a first hydride reducing agent of the compound of the formula X to give a compound of the formula IX is conducted with a borohydride reducing agent, such as calcium borohydride or sodium borohydride. In an embodiment of the present invention, the reduction of the compound of the formula X to give the compound of the formula IX is conducted with sodium borohydride in the presence of calcium chloride in ethanol solvent.

In an embodiment of the present invention, the reduction with a second hydride reducing agent of the compound of the formula IX to give a compound of the formula VIII is conducted with a metal hydride reducing agent, such as lithium aluminum hydride or lithium borohydride.

In an embodiment of the present invention, the protecting the free amine in the compound of the formula VII with an amino protecting group to give a compound of the formula VI, the amino protecting group is a BOC protecting group or a CBZ protecting group.

In an embodiment of the present invention, in the step of contacting a compound of the formula VI with tosyl chloride to give a compound of the formula V, the weak organic base is pyridine, triethylamine, or N,N-diisopropylethylamine.

In an embodiment of the present invention, in the step of contacting a compound of the formula II with a compound of the formula III to give the compound of the formula I, the coupling agent is 1-propyl phosphonic anhydride, oxalyl chloride or thionyl chloride.

In an embodiment of the present invention, in the step of contacting a compound of the formula II with a compound of the formula III to give the compound of the formula I, the weak organic base is di-isopropylethylamine, triethylamine, N-methylmorpholine, or di-aza-[2.2.2]bicyclo-octane.

In an embodiment of the present invention, in the step of contacting a compound of the formula II with a compound of the formula III to give the compound of the formula I, the reaction is conducted in dichloromethane, dichloroethene, acetonitrile, isopropanol, toluene, N,N-dimethylacetamide, dimethylformamide, or tetrahydrofuran solvent.

In another embodiment, the invention is directed to a process for preparing a compound of the formula I which comprises contacting a compound of the formula II with a compound of the formula XIV in the presence of a reagent that forms a metal amide of the compound of the formula II.

In an embodiment of the present invention, the reagent used to form the metal amide of a compound of the formula II is isopropylmagnesium chloride, butyllithium, or trimethylaluminum.

In an alternate embodiment, the present invention is directed to a process for preparing a compound of the formula III:

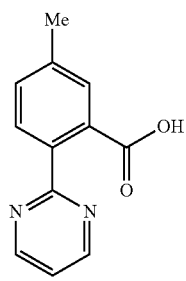

III which comprises:
contacting 2-iodo-5-methylbenzoic acid of the formula XVII

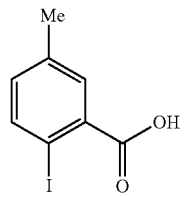

XVII with methanol in the presence of a strong acid to give methyl 2-iodo-5-methyl benzoate of the formula XVI:

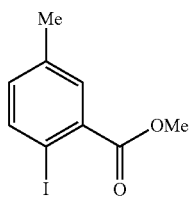

XVI followed by contacting the methyl 2-iodo-5-methyl benzoate of the formula XVI with pinacol borane or pinacolato diborane in the presence of palladium acetate, tri-O-tolylphosphine and a weak organic base to give a boronate compound of the formula XV:

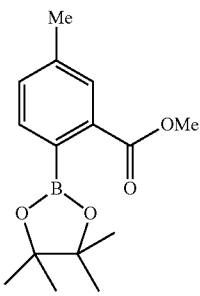

XV followed by contacting the compound of the boronate formula XV with 2-chloropyrimidine in the presence of PdCl$_2$ (dppf)-CH$_2$Cl$_2$ and a weak inorganic base to give the compound of the formula XIV:

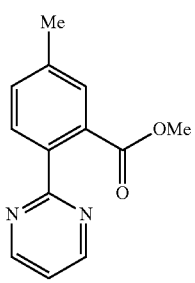

XIV followed by hydrolysis of the methyl ester with an inorganic base to give the compound of the formula III.

In an embodiment of the present invention, the step of contacting the step of contacting a compound of the formula XVI with pinacol borane in the presence of palladium acetate, tri-O-tolylphosphine and a weak organic base to give a boronate compound of the formula XV is conducted by adding the palladium reagent to the reaction mixture after the other reagents have been combined.

In an embodiment of the present invention, the step of contacting the boronate of formula XV with 2-chloropyrimidine to give the compound of formula XIV is conducted with PdCl$_2$(dppf)-CH$_2$Cl$_2$, PdCl$_2$(PPh$_3$)$_2$, or PdCl$_2$dppb in the presence of Na$_2$CO$_3$, K$_2$CO$_3$, or NaHCO$_3$.

A specific embodiment of an alternate aspect of the present invention is directed to a process for preparing a compound of the formula I:

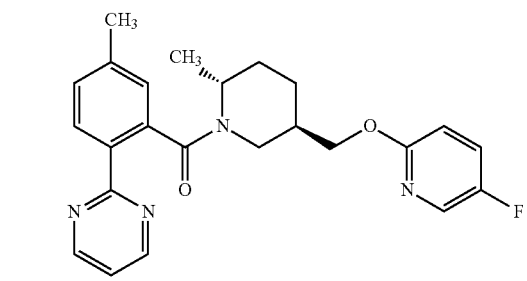

or a pharmaceutically acceptable salt thereof,
which comprises:

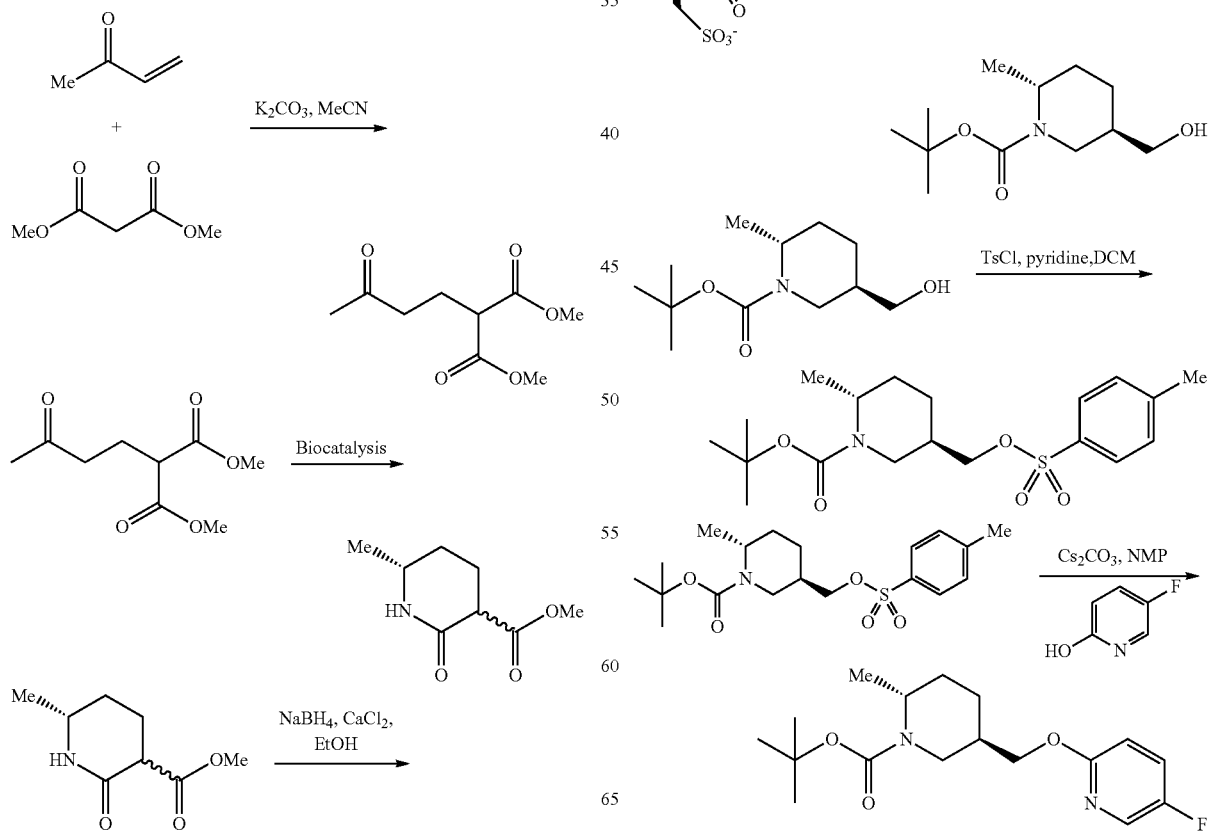

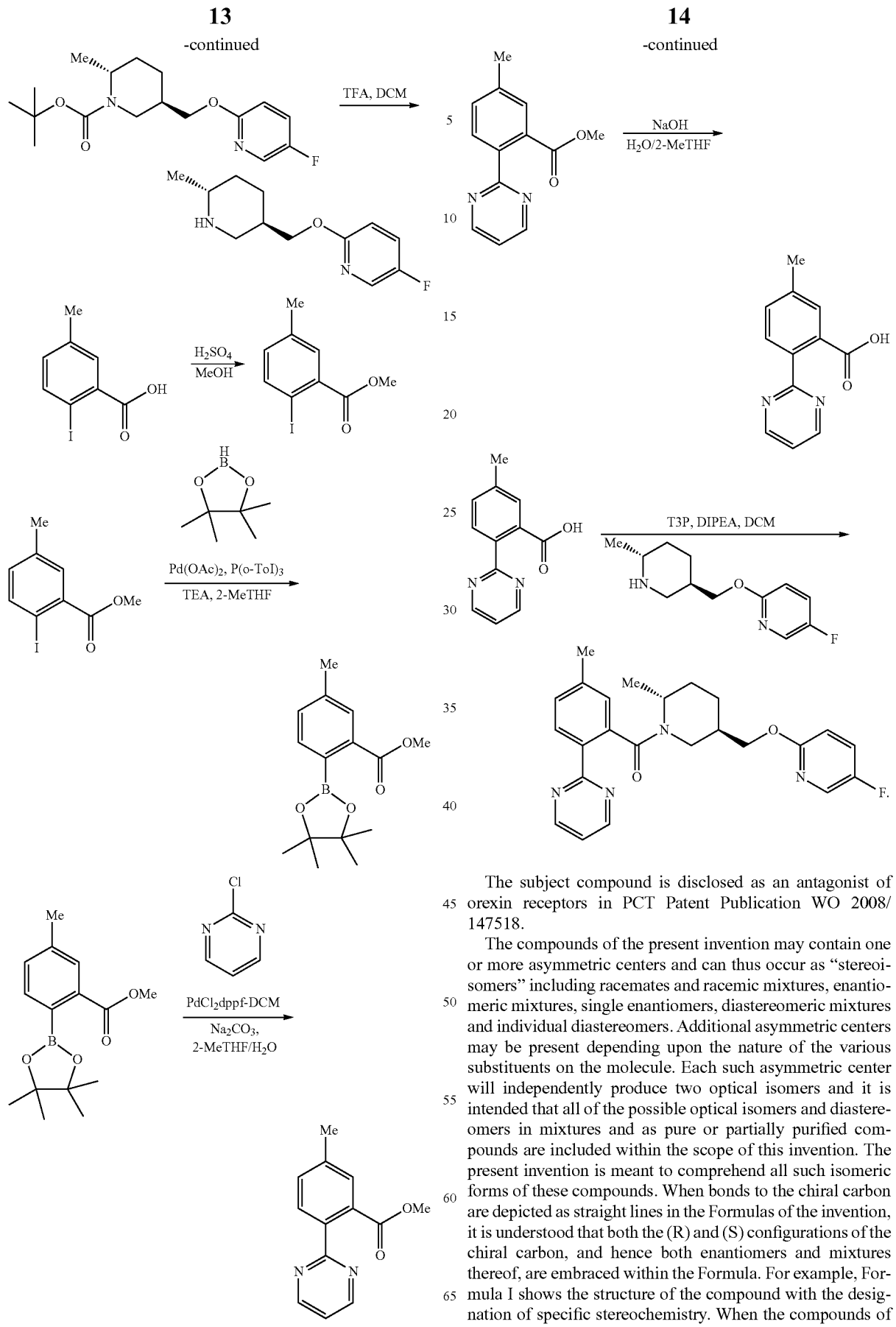

The subject compound is disclosed as an antagonist of orexin receptors in PCT Patent Publication WO 2008/147518.

The compounds of the present invention may contain one or more asymmetric centers and can thus occur as "stereoisomers" including racemates and racemic mixtures, enantiomeric mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the scope of this invention. The present invention is meant to comprehend all such isomeric forms of these compounds. When bonds to the chiral carbon are depicted as straight lines in the Formulas of the invention, it is understood that both the (R) and (S) configurations of the chiral carbon, and hence both enantiomers and mixtures thereof, are embraced within the Formula. For example, Formula I shows the structure of the compound with the designation of specific stereochemistry. When the compounds of the present invention contain one chiral center, the term "stereoisomer" includes both enantiomers and mixtures of enantiomers, such as the specific 50:50 mixture referred to as a racemic mixtures.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

As appreciated by those of skill in the art, halogen or halo as used herein are intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-8}$alkyl specifically includes methyl, ethyl, n-propyl, iso-propyl, n-butyl, iso-butyl, tett-butyl, pentyl, and hexyl. A group which is designated as being independently substituted with substituents may be independently substituted with multiple numbers of such substituents.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particular embodiments include the ammonium, calcium, magnesium, potassium, and sodium salts. Salts in the solid form may exist in more than one crystal structure, and may also be in the form of hydrates, Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments include the citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Several methods for preparing the compounds of this invention are illustrated in the following Schemes and Examples. Starting materials are made according to procedures known in the art or as illustrated herein. The following abbreviations are used herein: 2-MeTHF: 2-methyltetrahydrofuran; Ac: acetyl; Ar: aryl; AY: assay yield; Bn: benzyl; Boc: tert-butyloxy carbonyl; Boc$_2$O: di-tert-butyldicarbonate; BSA: bovine serum albumin; Cbz: carbobenzyloxy; CDI: carbonyl diimidazole; CSA: camphor sulfonic acid; DEAD: diethylazodicarboxylate; DCE: dichloroethane; DCM: dichloromethane; DIPEA: N,N-diisopropylethylamine; DMF: N,N-dimethylformamide; DMSO: dimethylsulfoxide; EDC: N-(3-dimethylaminopropyl)-N'-ethylcarbodiimide; Et: ethyl; EtOH: ethanol; Et$_3$N: triethylamine; GC-FID: gas chromatography-flame ionization detector; HOBT: hydroxybenzotriazole hydrate; HPLC: high performance liquid chromatography; LC-MS: liquid chromatography-mass spectrometry; LRMS: low resolution mass spectrometry; Me: methyl; MTBE: methyl tert-butyl ether; NAD: nicotinamide adenine dinucleotide; NMP: N-methylpyrrolidone; PdCl$_2$(dPPf)-CH$_2$Cl$_2$: [1,1'-Bis(diphenylphosphino)ferrocene] dichloropalladiuna(II) dichloromethane; Ph: phenyl; PhMe: toluene; PLP: pyridoxal-5' phosphate; rt: room temperature; SOCl$_2$: thionyl chloride; T3P: 1-propylphosphonic anhydride; t-Bu: Cert-butyl; TsCI: tosyl chloride; TFA: trifluoracetic acid; THF: tetrahychofuran. The compounds of the present invention can be prepared in a variety of fashions.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes and examples may be varied to facilitate the reaction or to avoid unwanted reaction products. The following examples are provided so that the invention might be more fully understood. These examples are illustrative only and should not be construed as limiting the invention in any way.

EXAMPLE A

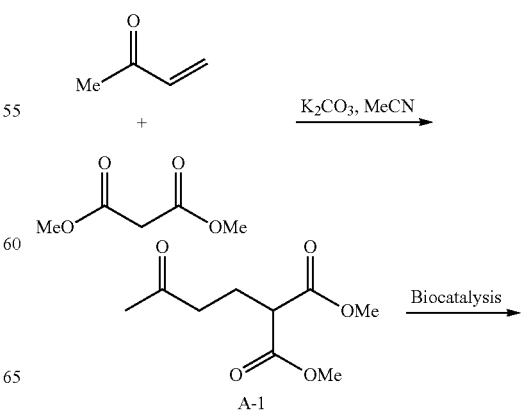

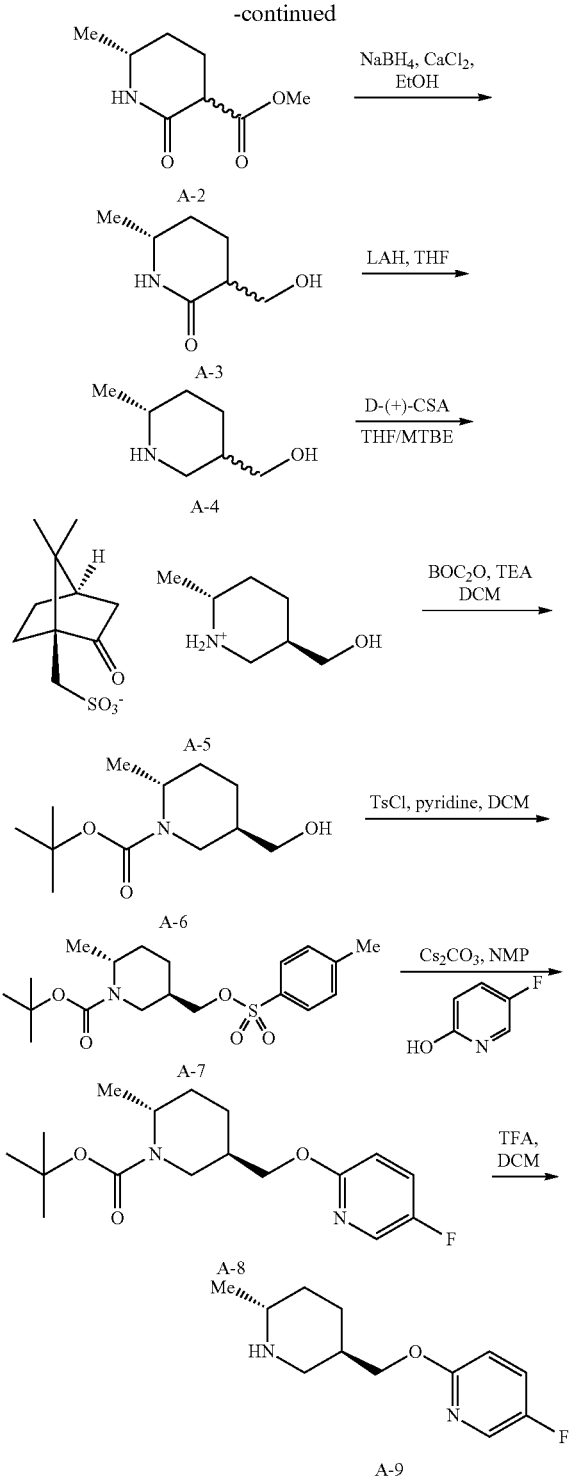

Dimethyl (3-oxobutyl)malonate (A-1)

To a visually clean and dry 100 L round bottom flask equipped with an addition funnel, a nitrogen inlet and a thermocouple were added acetonitrile and potassium carbonate. Dimethyl malonate was added and the resulting mixture was cooled to 17° C. (ice/water bath). The methyl vinyl ketone was added over 3 h with the internal temperature not rising above 26° C. After 18 h, HPLC showed full conversion. The mixture was transferred to a 100 L extractor charged with 60 L MTBE and 20 L water. The layers were separated and the aqueous layer was back extracted with 20 L MTBE. The combined organic layers were washed with 20 L water, allowing 5 h for the emulsion to settle. The organic layer was then filtered through activated carbon and batch concentrated, flushing with 20 L MTBE to afford 15.1 kg of A-1 (80 wt % by $^1$H NMR, 80% yield). Data for A-1: $^1$H NMR (400 MHz, CDCl$_3$) δ 3.69 (s, 6H), 3.40 (t, J=7.3 Hz, 1H), 2.50 (t, J=7.2 Hz, 2H), 2.15-2.06 (m, 5H).

Dimethyl(3-oxobutyl)malonate (A-1)

Potassium carbonate (5.62 kg), dimethyl malonate (54.8 kg) and acetonitirile (90 kg) were charged to the reaction vessel and stirred together at 15° C. Methyl vinyl ketone (28.5 kg) was pumped into the vessel over 2 hours at below 25° C. The slurry was stirred at 18-20° C. for 2 hours. MTBE (132 kg) was charged to the vessel to dilute the reaction mixture followed by water (114 kg). The mixture was stirred for five minutes then the layers were allowed to separate and the aqueous layer run off. More water (57 kg) was charged to the vessel, the reaction mixture stirred for another 5 minutes, the layers allowed to separate, and again the aqueous layer run off. The organic layer was concentrated under reduced pressure until most of the solvent had been removed (volume approx 80 L) affording 76 kg of A-1 as an oil.

Methyl (6R)-6-methyl-2-oxopiperidine-3-carboxylate (A-2)

To a visually clean 20 L round bottom flask was charged 7.15 kg of 64 wt % A-1 and rotary evaporated to remove residual acetonitrile and MTBE. The resulting solution was 83 wt %. To a visually clean 100 L Buchi jacketed reactor with overhead stirring was added 45 L water. Heating to 30° C. was initiated, followed by addition of 852 g Na$_2$HPO$_4$, 7.2 kg D-alanine, 6.48 kg Glucose, 22.5 g NAD, and 45 g PLP. The pH was adjusted to 7.4 with NaOH and then 450 g ATA-117 transaminase, 9 g Lactate Dehydrogenase, and 45 g glucose dehydrogenase were added and rinsed into the vessel with 2.5 L water. After all enzymes were in solution, the rotavaped solution of A-1 was added, followed by a final 2.5 L water. pH control utilizing 5 N NaOH was initiated. The reaction was allowed to stir for 42 hours; the reaction was complete at 31 hours. To the reaction vessel were added 19.4 kg NaCl and 6.0 L 5N HCl to adjust the pH to 3.5. 20 L of acetonitrile was added and allowed to stir for 10 min. The agitator was turned off and the reaction mixture allowed to settle for 1 h. The acetonitrile layer was drummed off; the aqueous layer was re-extracted with acetonitrile, and these acetonitrile layers were combined. The resulting acetonitrile solution was filtered through Solka-Floc and combined with a second batch of similar size and batch concentrated to remove both acetonitrile and water. The resulting oil contained high levels of heterogeneous NaCl. The oil was then dissolved in 50 L EtOAc and transferred to a visually clean 20 L round bottom flask and rotavaped to provide A-2 as an oil (5.5 kg, 94 wt %, 74% yield, 99% ee determined by HPLC on Chiralpak). Data for A-2: LRMS (MSH)=172.

Methyl (6R)-6-methyl-2-oxopiperidine-3-carboxylate (A-2)

Water (516 kg) was charged to a 1000 L vessel followed by disodium hydrogen orthophosphate (36.3 kg), D-alanine (41.8 kg) and D-glucose (37.6 kg). The mixture was warmed to 30° C. to dissolve the solids. NAD (130.5 g) and PLP (261 g) were added and the pH checked (7.8). ATA-117 transaminase (2.61 kg), lactate dehydrogenase (52.2 g), and finally glucose dehydrogenase (130.5 g) were added and rinsed into the vessel with 2.5 L water. After all enzymes were in solution, A-2 (39.2 kg total, 29 kg assay) was added, followed by a final water rinse (5 kg). The reaction mixture was stirred at 30° C. with the pH being adjusted to pH 7.6 every 2-3 hours by the addition of 5N NaOH for the first 6 hours. The reaction was then left to stir overnight (16 hours) before the pH was again adjusted to pH 7.6. The reaction was allowed to stir for 44 hours. Sodium chloride (90 kg) was added to the reaction mixture and the pH adjusted to pH 3.6 by the addition of 5N HCl (66 L). Dichloromethane (200 kg) was charged to the vessel followed by solka-Flok (15 kg) and the mixture allowed to stir for 10 minutes. The batch was then filtered through more Solka-Flok (5 kg). The Solka-Flok was washed with more dichloromethane (65 kg). The filtrates were returned to the vessel, and the layers allowed to separate. The lower organic layer was run off and the aqueous layer re-extracted with dichloromethane (200 kg). The lower organic layer was run off and the aqueous layer discarded. The organic layers were recombined, returned to the vessel and washed with 8% sodium bicarbonate solution (54 L) for 20 minutes. The layers were allowed to separate and the organic layer run off. The aqueous layer was discarded and the organic layer returned to the vessel. The dichloromethane solution of A-2 (19.3 kg assay) was stored at room temperature until required.

(6R)-3-(Hydroxymethyl)-6-methylpiperidin-2-one (A-3)

A visually clean and dry 140 L extractor, equipped with glycol cooling coils, nitrogen inlet, large gas exit and thermocouple was charged with an 18.7 wt % solution of A-2 in EtOH [4.6 L/kg] and an additional 71.4 L EtOH [25.4 L/kg]. Calcium chloride (3.65 kg) was added in 3 portions over 15 min and stirred until complete dissolution with cooling from 26 to 22° C. Sodium borohydride (2.49 kg) was added in 3 portions over 20 min. After the last addition, the temperature increased to 25° C. Gas evolution subsided within 30 min. The reaction mixture was allowed to stir for 20 h with the cooling set to keep the temperature below 22° C. The mixture was cooled to 5° C. and was quenched by careful addition of 11.2 L 6 N HCl over 30 min, keeping the temperature below 9.5° C. It was warmed to room temperature and stirred for 2 h. Wet pH paper dipped in the mixture showed pH 2. It was filtered over Solka-Floc and rinsed with 2×12 L EtOH. Each bin was assayed for a total of 2.55 kg (108% AY). The filtrate was combined with a second batch of similar size for batch concentration. After most of the ethanol was evaporated, 8 L of water were added to coevaporate EtOH and partially solubilize precipitate. After transferring the 23 L aqueous layer to the extractor, the volume was adjusted with water to 31.6 L. It was extracted with 53 L then 2×26.5 L 1-butanol (HPLC assay shows 92 g, 1.9% losses in the aqueous layer). The combined organic layers were washed with 10.5 L brine (HPLC assay shows 419 g, 8.8% losses to the wash). The organic layer was assayed to 4.21 kg (92% recovery, 96% AY) and concentrated to a minimum volume. It was then azeotroped with 12 L water, then 120 L isopropanol. The KF was assayed to 0.5% water on a total volume of ~40 L. The suspension was filtered over Solka-Floc and rinsed with 2×10 L isopropanol. The filtrate was stirred in the extractor to homogenize it and was assayed to 4.13 kg (94% AY, 1.7:1 dr). The solution was separated in two equal batches. Each batch was concentrated to a minimum volume and azeotroped with 140 L THF to yield A-3 as a beige suspension. (94% yield). $^1$H NMR shows 0.6 eq isopropanol. Data for A-3: LRMS (MSH) =144.

[(6R)-6-methylpiperidin-3-yl]methanol (A-4)

A visually clean and dry 100 L 5-neck round-bottom flask equipped with a mechanical stirrer, a thermocouple, a nitrogen inlet and a cooling bath was charged with A-3 (2.07 kg, 1.0 eq) and THF (20 L, 10 mL/g). The mixture was cooled to −25° C. The LiAlH4 (2.6M soln, 22.2 L, 4.0 eq) was added over a period of 3.5 h, keeping the mixture between −25° C. and +12° C. An important gas evolution (H$_2$) was observed during the addition of the first 6 L of LiAlH$_4$. Upon completion of the addition, the mixture was allowed to warm to 20° C., then heated using steam to 50° C. The mixture was aged at this temperature for a period of 12 h. GC-FID and LC-MS showed >99% conversion to the desired piperidine-alcohol. The mixture was cooled to −25° C., and the reaction was quenched using the Fieser work-up. Water (2.2 L) was added over 3 h to the mixture, creating an important gas evolution and exotherm (temperature was kept between −25° C. and +13° C.). 3.75M NaOH (2.2 L) was then added to the mixture over a period of 1.5 hrs. Finally, water (6.6 L) was added over a period of 1 hr. The mixture was cooled to 5° C. and aged 1.5 h. The suspension was filtered, and the cake was rinsed with THF (20 L). 1.54 kg (2.33% wt) were obtained, therefore the assay yield of A-4 was 82% (dr=1.7:1, favoring the trans isomer). Data for A-4: LRMS (M+H)=130.

[(3R,6R)-6-methylpiperidin-3-yl]methanol-CSA salt (A-5)

A visually clean and dry 140 L 5-neck extractor equipped with a mechanical stirrer, a thermocouple, a nitrogen inlet and a cooling coil was charged with A-4 (3.04 kg, 1.0 eq) and THF (60 L, 20 mL/g). To the mixture was added a THF solution (4 mL/g, 12 L) of (D)-(+)-CSA (4.37 kg, 0.8 eq) over a period of 1 h. The salt crystallized out without seeding. Upon completion of the addition, the mixture was aged 45 min at 20° C., then MTBE (10 mL/g, 30 L) was added over 45 min. The mixture was aged for 45 min, then cooled to 2° C. over 45 min. The mixture was aged at this temperature for a period of 30 min, then filtered. The salt was rinsed 2×6 mL/g (2×18 L) with THF/MTBE 1/1, then 1×6 mL/g (1×18 L) MTBE, and was dried on the fit under a nitrogen atmosphere for a period of 16 h to provide 4.46 kg (52% yield) of A-5 as a white solid. The diastereoselectivity of the salt (measured on a free base sample after salt break) was 40-50:1.

[(3R,6R)-6-methylpiperidin-3-yl]methanol-CSA salt (A-5)

Crude A-2 (40 g assay; 55.94 g total) was dissolved in THF (773 mL). Ethanol (43.1 g) was added to the solution and the solution cooled to 0° C. LiBH4 (228 ml; 4.1M in THF) was added over 30 minutes at below 5° C. and mixture was stirred at RT. Mixture was warmed to 20° C. and stirred overnight. The reaction mixture was cooled to 10° C. and added 6M HCL (240 mL) with care over 30 minutes. The white cloudy mixture was stirred at 20° C. for 2 hours. pH of mixture: pH=1. The pH of the reaction mixture was adjusted to pH 12-14 by the addition of 10 M NaOH (120 mL) and isopropyl acetate (120 mL) added. The layers were separated and the aqueous layer re-extracted with isopropyl acetate (2×240 mL). The organic layers were combined and evaporated to residue. The oily residue was flushed with isopropanol (3×200 mL) to give a water content of <200 μL/mL. The crude oil was then dissolved in THF (450 mL). Solvent analysis gave no IPAc present, <1% IPA present. A solution of D-(+)-camphorsulfonic acid (54.3 g) in THF (130 mL) was added over 30 minutes to the THF solution of the piperidinol. A white solid crystallized. The mixture was stirred at 20° C. overnight. The slurry was diluted with MTBE (300 mL) and the mixture was cooled to 0° C. for 2 hours before filtering. The solid was washed with 1:1 THF:MTBE (100 mL) and MTBE (100 mL). The solid was dried in vacuo at 45° C. overnight to give A-5 as a white solid (39.7 g) in 47% yield, diastereomer ratio: 20:1 trans:cis (NMR)

tert-butyl (2R,5R)-5-(hydroxymethyl)-2-methylpiperidine-1-carboxylate (A-6)

A visually clean and dry 140 L extractor, equipped with glycol cooling coils, nitrogen inlet, and thermocouple was charged with 40 L of dichloromethane followed by A5 (4.2 kg). To this suspension was added triethyamine in one portion (4.8 L, no exotherm observed) followed by $Boc_2O$ (2.66 kg added over 5 min, 4° C. exotherm observed). After 30 minutes, the reaction mixture became homogeneous. An LCMS assay (after 3 h) showed complete consumption of the starting material. The reaction mixture was diluted with ammonium chloride 2 M (40 L) and the layers were separated. The organic layer was washed with half saturated brine (20 L) and the layers were separated. An HPLC assay of the crude reaction mixture indicated a 105% AY (2.81 kg). This crude reaction mixture was dried over $Na_2SO_4$ (200 wt %), filtered and transferred into a 100 L flask for the tosylation reaction.

tert-butyl (2R,5R)-2-methyl-5-({[(4-methylphenyl)sulfonyl]oxy}methyl)piperidine-1-carboxylate (A-7)

A Visually Clean and Dry 100 L Reactor Equipped with a Mechanical Stirrer, a nitrogen inlet and a thermocouple was charged with the crude dichloromethane solution of A-6 (final volume was adjusted to 10 L, approximatly 2.2 mL/g). To this cold solution (0° C.) was added pyridine (5.5 L, no exotherm observed) followed by TsCi (in 4 portions over 1 h, exotherm observed but easily controlled). The reaction mixture was warmed to room temperature and stirred for 18 h (HPLC showed complete consumption of the starting material). The reaction mixture was transferred into a 140 L extractor and diluted with MTBE (7 mL/g), $NH_4Cl$ sat. (20 L) and water (10 L). The layers were separated and the organic layer was washed with $CuSO_4.5H_2O$ (20 L followed by 10 L), sat $NaHCO_3$ (10 L) and half saturated brine (10 L). The crude organic layer was filtered on a pad of silica gel (1.5 kg) and the pad was rinsed with MTBE (10 L). The assay yield of A-7 measured on the resulting solution was 93% (4.28 kg). Data for A-7: LRMS (M-Boc)=284.0.

tert-butyl (2R,5R)-5-{[(5-fluoropyridin-2-yl)oxy]methyl}-2-methylpiperidine-1-carboxylate (A-8)

A visually clean and dry 100 L 5-neck round-bottom flask equipped with a mechanical stirrer, a thermocouple, a nitrogen inlet and a cooling bath was charged with A-7 (3.23 Kg, 1.0 eq) and NMP (65 L, 20 mL/g). 5-Fluoro-2-hydroxypyridine (1.19 kg, 1.25 eq) was added, followed by the addition of the $Cs_2CO_3$ (7.37 Kg, 2.7 eq). No exotherm was observed. The mixture was warmed to 60° C. and aged at this temperature for a period of 26 h. HPLC showed >99.9% conversion to the desired product. The mixture was cooled to 15° C., the reaction was quenched by the addition of water (65 L), added over 1 h to control the exotherm (15° C. to 28° C.). The piperidine-O-pyridine was extracted using MTBE (20 mL/g, 65 L). The organic layer was washed 2×10 mL/g 10% LiCl (2×32 L), then 2×10 mL/g NaCl half saturated solution (2×32 L). The assay yield of A-8, measured on the MTBE layer, was 2.16 kg, 79% yield. Data for A-8: HRMS (M+H)=325.1922.

5-fluoro-2-{[(3R,6R)-6-methylpiperidin-3-yl]methoxy}pyridine (A-9)

A visually clean 50 L flask equipped with a thermocouple and mechanical stirrer was charged with a solution of A-8 (2.15 kg, 6.63 mol) in MTBE which was solvent switched to dichloromethane (11.40 L). This mixture was cooled to −2° C. with an ice/IPA bath. TFA (5.5 L, 71.4 mol) was then added slowly (over 40 minutes, T ° C.=−1.9° C. to 5.5° C., max 5.5° C.). Once addition was completed, the reaction was removed from the ice bath and warmed to room temperature with warm water (start 5.7° C., 50 minutes). The reaction was completed within 3.5 h. Concentration under reduced pressure and transfer of the resulting oil to a cooled stirring solution of NaOH (3.0 N, 1.1 eq., 28 L) in a 100 L extractor was followed by addition of 30 L of MTBE and the phases were separated. The organic layer was washed with 30 L of 2 N HCl and again with 10 L of 2 NHCL The aqueous layers were then cooled (9° C.) and 10 N NaOH was added until the pH was 13 (T°=21° C.). To this solution was added 25 L of MTBE and the layers were cut. Finally, the aqueous layer was back-extracted with 10 L of MTBE. Quantitative HPLC assay revealed 98% yield and >99.7% purity of A-9 used as is a subsequent reaction. Data for A-9: LRMS (M+H)=225.1.

5-fluoro-2-{[(3R,6R)-6-methylpiperidin-3-yl]methoxy}pyridine (A-9)

A 3-L, three-necked, round-bottomed flask equipped with a septum, nitrogen inlet adapter, mechanical stirrer, and thermocouple was charged with A-5 (87.0 g), 2,5-difluoropyridine (30.0 g), and 870 mL of DMSO (110 ppm water) at room temperature (23° C.). Sodium t-butoxide (50.1 g) was added portion wise over 4 min keeping the internal temperature below 29° C. The resulting reaction mixture was stirred at room temperature (ea. 25° C.) until HPLC analysis indicated less than 5% difluoropyridine compared to the desired product. (Agilent Eclipse XDB-C18 4.6×150 mm column; 35° C.; Mobile phase: (A) 0.1% $H_3PO_4$/water; (B) Acetonitrile. Linear gradient, Time 0: 95% A, 5% B; Time 6 min: 5% A, 95% B; Time 10 min: 5% A, 95% B. Flow rate, 1.5 mL/min. UV=210 tun; A-5 RT=2.8 min, A-9 RT=3.2 min, 2,5-difluoropyridine RT=4.1). The reaction mixture was then diluted with water (20 vol., 1740 mL) and EtOAc (10 vol., 870 mL). The organic layer was separated, washed with water (10 vol., 870 mL), and transferred to a 2-L round-bottomed flask. HCl (3.9 N solution in IPA) was slowly added via addition funnel over 30 min and the resulting white slurry was stirred at room temperature for 1 h. The crystals were collected, washed with EtOAc (3 vol., 2610 mL), and dried under vacuum with a nitrogen sweep to give 55.0 g of A-9 as white crystals.

EXAMPLE B

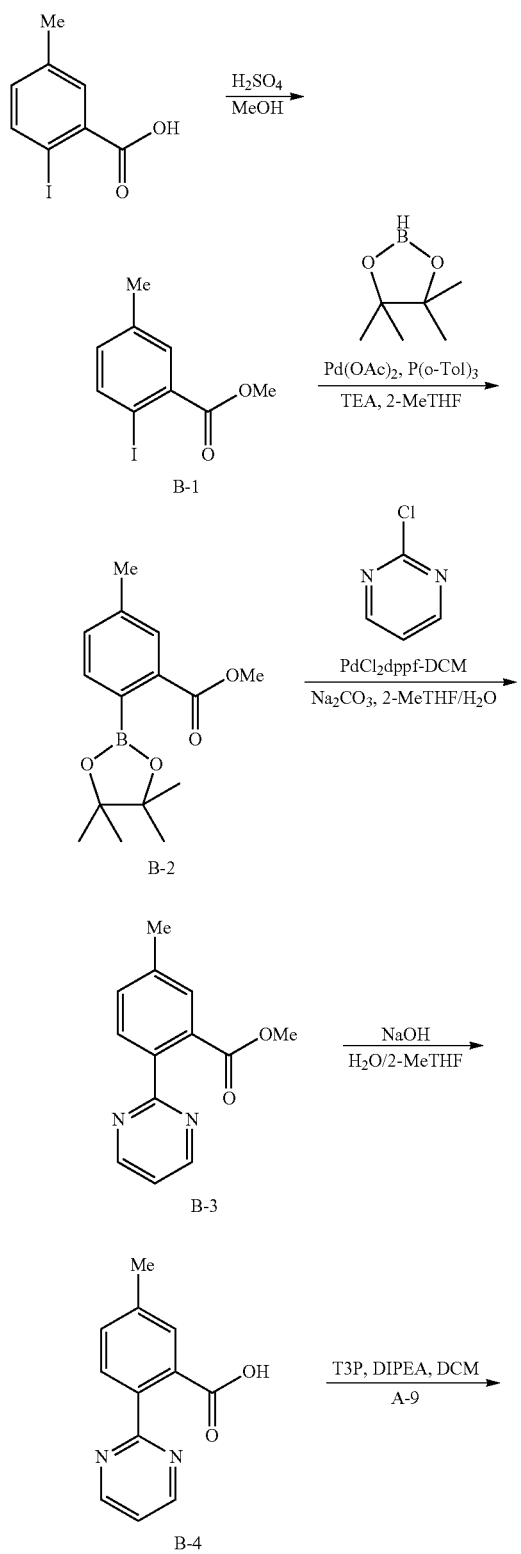

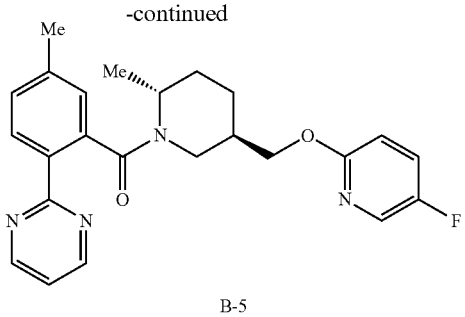

B-5

Methyl 2-iodo-5-methylbenzoate (B-1)

A visually clean 100 L flask equipped with a mechanical stirrer thermocouple and water chilled condenser was charged with MeOH (50 L). 2-iodo-5-methylbenzoic acid (5.85 kg, 22.32 mol) was then added while stirring. Concentrated sulfuric acid (0.595 L, 11.16 mol) was then added portion-wise which caused an increase in temperature from 17° C. to 22° C. This mixture was gradually brought to an internal temperature of 64.6° C. and aged overnight (~18 h). The next morning the reaction had reached >98% conversion by HPLC. The flask was cooled to 16° C. by placing in an ice bath and 850 mL of 10 N NaOH (0.98 equiv.) was added slowly (over 10 minutes) while monitoring the pH. After the addition the pH was 5-6 (caution: bringing pH over 9 can result in saponification during the work-up). The solution was then concentrated to about 16 L and this suspension was transferred to a 100 L extractor. The flask was rinsed with 8 L of IPAc and 4 L of water which were also transferred to the extractor. 32 L of IPAc were added along with 10 L of 5 w % NaHCO$_3$ and 10 L of 15 w % Brine. The layers were cut and the aqueous layers were back-extracted with 20 L of IPAc. The organic layers were then combined and washed with 10 L of 15 w % Brine. The organic layers were collected to provide B-1 (6.055 kg, 2193 mol, 98% yield) in 98.3% purity. $^1$H NMR (500 MHz, CDCl$_3$, 293K, TMS): 7.84 (1 H, d, =8.07 Hz), 7.62 (1 H, d, J=2.14 Hz), 6.97 (1 H, dd, J=8.08, 2.14 Hz), 3.97-3.86 (3 H, m), 2.33 (3 H, s).

Methyl 5-methyl-2-(4,4,5,5-tetramethyl-1,3,2-dioxaborolan-2-yl)benzoate (B-2)

A solution of B1 (5.9 kg, 21.37 mol) in iPAc was charged in a visually clean 100 L reactor equipped with a mechanical stirrer and thermocouple. The solution was solvent switched to 2-MeTHF (~35 L). Triethylamine (8.94 L, 64.1 mol) was added and the solution was degassed with N$_2$. Pinacol borane (4.65 L, 32.1 mol) was added slowly (over 15 mins) to the stirring solution while maintaining the purge. The solution was further degassed for 10 min and tri-o-tolylphosphine (0.325 kg, 1.069 mol) was added followed by palladium (II) acetate (0.120 kg, 0.534 mol). This caused the reaction to turn black immediately with a slow exotherm from 11.5° C. to 30° C. At this point a delayed exotherm was observed and the reaction temperature increased to 60° C. (over 45 min). The reaction temperature was increased to 77° C. and aged for another 45 min. At this point, HPLC analysis of a reaction aliquot revealed complete consumption of the starting material. The heat source was removed and an ice bath was placed under the flask to cool the reaction over 1.5 h. A 26 w % ammonium chloride solution was added very slowly to control gas evolution and exotherm (over 60 minutes) which caused a black precipitated to form. The supernatant was transferred to an extractor which already contained 40 L of water. The black slurry remaining was filtered on Solka-Floc and washed with MTBE (~20 L). The filtrate was loaded into the extractor. The layers were cut and assay of the organic layers revealed B-2 (4.45 kg, 16.11 mol, 75% yield) in 81.6% purity and was used as is in the following step. $^1$H NMR (500 MHz, CDCl$_3$, 293K, TMS): 7.75 (1 H, s), 7.40 (1 H, d, J=7.49 Hz), 7.32 (1 H, d, J=7.56 Hz), 3.90 (3 H, s), 2.37 (3 H, s), 1.41 (12 H, s).

Methyl 5-methyl-2-pyrimidin-2-ylbenzoate (B-3)

A solution of B-2 (4.38 kg, 15.84 mol) from the previous reaction was charged in a visually clean 100 L reactor equipped with a mechanical stirrer and a thermocouple. The mixture was solvent switched to 2-MeTHF (35 L). This was followed by addition of 2-chloropyrimidine (2.18 kg, 19.01 mop (endothermic 19 to 14° C.) and sodium carbonate (5.04 kg, 47.5 mal), To this stirring suspension was added water (11.67 L) (exothermic 15-24° C.). The thick slurry was degassed with N$_2$ for 40 minutes after which PdCl$_2$(dppf)-CH$_2$Cl$_2$ adduct (0.518 kg, 0.634 mol) was added which causes the reaction to become black. The internal temperature was set to 74° C. and aged for 16 h. An aliquot was taken for HPLC analysis and revealed near complete consumption of the starting boronate (>97% conv.). The reaction was cooled to room temperature, and 12 L of water and 24 L of MTBE were added while maintaining stirring for 10 minutes. This solution was filtered on Solka-Floc and transferred to a 100 L extractor. The flask was further rinsed with 4 L of both MTBE and water (×2) and then another 4 L of MTBE. The layers were cut and the aqueous layers were back-extracted with 21.5 L of MTBE. Assay of the organic layers showed the biaryl ester (2.76 kg, 12.09 mol, 76% yield). The organics were reloaded into the extractor and 1.26 kg of activated carbon (Darcy KB-G grade) was added and the mixture was stirred for 2 h and then filtered over Solka-Floc. The filter cake was washed with 3×10 L of MTBE. Heavy metal analysis revealed 427-493 ppm of Pd and 882-934 ppm of Fe. Assay was 2.381 kg of B-3 (66% overall, 86% recovery from DARCO). Data for B-3: $^1$H NMR (500 MHz, CDCl$_3$, 293K, TMS): 8.78 (d, T=4.87 Hz, 2 H); 7.97 (d, 3=7.93 Hz, 1 H); 7.51 (s, 1 H); 7.39 (d, 3=7.99 Hz, 1 H); 7.19 (t, 3=4.88 Hz, 1 H); 3.75 (s, 3 H); 2.44 (s, 3 H).

5-Methyl-2-pyrimidin-2-ylbenzoic acid (B-4)

A solution of B-3 from the previous step was charged to a visually clean 100 L flask through an in-line filter, concentrated and solvent switched to 2-MeTHF (~15 L). To this solution was added water (20 L) and then sodium hydroxide (10 N) (2.60 L, 26.0 mol). After the addition the reaction turned red and the heat source was set to 72° C. The mixture was aged at this temperature for 1.5 h after which complete conversion was observed by HPLC analysis. The reaction was cooled and transferred to a 50 L extractor. The flask was rinsed with 4 L of water and 10 L of MTBE which was added to the stirring mixture in the extractor. The layers were cut, and the aqueous phase was washed twice with 10 L of MTBE. The aqueous layer was then re-introduced into the reactor (100 L) through an in-line filter for the acidification. 2.3 L of 12 N HCl was added slowly to the cold mixture which causes an exotherm from 7 to 10° C. This caused a beige precipitate to form (pH=1). This precipitate was filtered. The beige filter cake was washed twice with 3 mL/g of cold water. Then the cake was washed with 3 mL/g of cold 15% MTBE/Heptane and 15% PhMe/Heptane. Finally it was washed with 1.5 mL/g of room temperature MTBE and twice with room temperature 3 mL/g Heptane. The solid was then dried under a stream of N$_2$ for 2 days to provide B-4 as a light beige powder (2.15 kg, 10.04 mol, 97% yield). HPLC analysis reveals the product to be 99.2% purity. Heavy metal analysis revealed 264 ppm of Pd and 19.7 ppm of Fe. Data for B-4: $^1$H NMR (500 MHz, DMSO-d$_6$): 12.65 (s, 1 H); 8.85-8.82 (m, 2 H); 7.78 (dd, J=7.89, 2.34 Hz, 1 H); 7.49-7.37 (m, 3 H); 2.40 (s, 3 H).

2-{2-[((2R,5R)-5-{[(5-Fluoropyridin-2-1 oxy]methyl}-2-methylpiperidin-1-yl)carbonyl]-4-methylphenyl}pyrimidine (B-5)

The solution of A-9 (1 kg, 4.46 mol) was charged in a visually clean and dry 50 L flask equipped with a thermocouple and mechanical stirrer and was solvent switched to DCM (11.00 L). DIPEA (2 L, 11.45 mol) is added and then B-4 (1.22 kg, 5.67 mol) was added to this stirring solution. This solution was cooled with an ice bath (12° C.). To this stirring solution was added T3P (7.87 L, 13.38 mol) through an addition funnel keeping the reaction temperature <21° C. over 1 h. Once addition was completed, the reaction became yellow and heterogenous. To facilitate stirring 2 L of DCM were added. The reaction was heated to 44° C. (small exotherm at 42° C., which caused the temperature to rise to 46.7° C. and maintain that temperature for 30 min). The reaction was aged at this temperature overnight. After 17 h the reaction was not complete and T3P (1.1 L, 1.870 mol) was added to accelerate conversion. The next day (42 h) the reaction was deemed complete by HPLC and was cooled in an ice bath to 4° C. 20 L of water was added (slowly for the first 1.5 L then pretty fast) keeping the reaction temperature under 17° C. This mixture was stirred at room temperature for 30 min. Then the mixture was transferred into a 50 L extractor charged with 20 L of MTBE. The flask was rinsed with an additional 2 L of water and 4 L of MTBE. The layers were cut and the organics are washed with 20 L 1N NaOH and then 10 L of 1N NaOH. Finally, the organics were washed twice with 10 L of brine 15%. The organic fractions (quantitative HPLC assay at 1.65 kg) were then treated with ~50 w % of Darco KB (750 g) for 1.75 h, filtered on Solka-Floc and rinsed with 10 mL/g of MTBE (1.559 kg, 94.5% recovery). To a visually clean and dry 50 L RBF equipped with a mechanical stirrer, a thermocouple, a reflux condenser and a nitrogen inlet was charged the crude material from above (B-5 solution and all solvents used were filtered using a 1 μm in-line filter). The reaction mixture was solvent switched to IPAc and the final volume was adjusted to 7.5 L (about 4 mL/g of IPAc). The reaction mixture was warmed to 75° C. (all soluble), cooled to room temperature slowly and seeded at 45° C. with 18 g of B-5 (in IPAc/heptane), stirred overnight (16 h) at room temperature, then heptane was added (6 mL/g) over 60 min. The reaction mixture was aged for 1 h before to be cooled to 5° C. and stirred for 30 min. The suspension was then transferred onto a filter pot and rinsed with IPAC/heptane (2×3 mL/g of cold 15% IPAc) and heptane (5 mL/g). The residual beige solid was dried under a flow of nitrogen for 18 h (the product was found to be dry with <0.3 wt % of solvents). 1.2 kg of B-5 was isolated as a light beige solid (99.4 LCAP, >99.5% ee, >99.5% dr, Pd level of 8 ppm and KF of 0.1). Data for B-5: HRMS m/z (M+H): 421.2067, found; 421.2035, required.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A process for preparing a compound of the formula I:

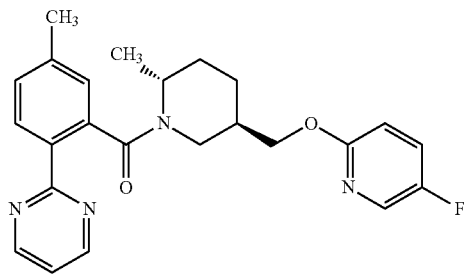

I or a pharmaceutically acceptable salt thereof,
which comprises:
contacting a compound of the formula II:

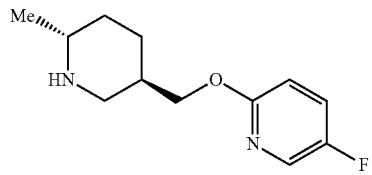

II with a compound of the formula III:

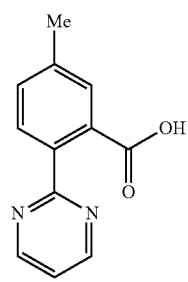

III in the presence of a coupling agent, which is selected from the group consisting of: 1-propyl phosphonic anhydride, oxalyl chloride and thionyl chloride;
to give the compound of the formula I, or a pharmaceutically acceptable salt thereof.

2. The process of claim 1 wherein the step of contacting the compound of the formula II with the compound of the formula III is conducted in the presence of a weak organic base.

3. The process of claim 2 wherein the weak organic base is diisopropylethylamine or triethylamine.

4. The process of claim 1 wherein the coupling agent is 1-propyl phosphonic anhydride.

5. A process for preparing a compound of the formula I:

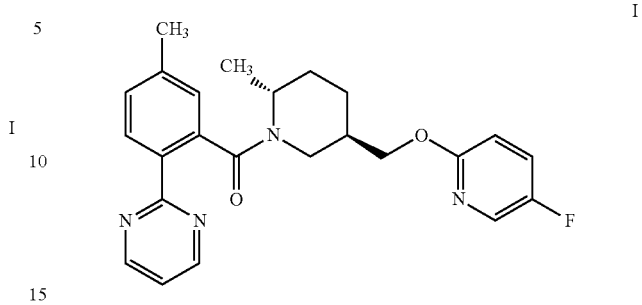

I or a pharmaceutically acceptable salt thereof,
which comprises:
contacting a compound of the formula V:

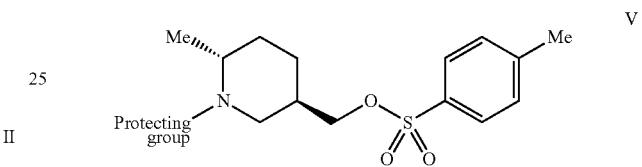

V with 5-fluro-2-hydroxypyridine of the formula VI:

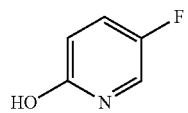

VI in the presence of cesium carbonate to give the compound of the formula IV:

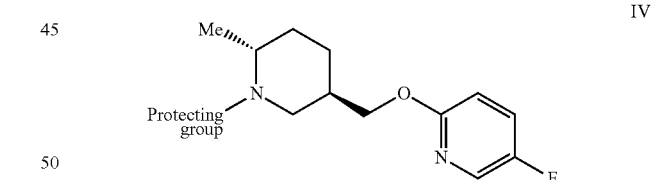

IV followed by removal of the protecting group in the compound of the formula IV to give the compound of the formula II:

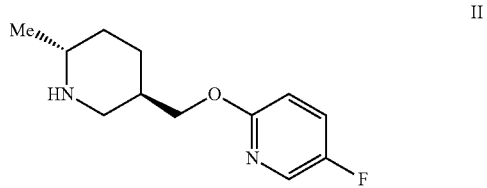 [SMILES: C[C@@H]1CC[C@@H](COc2ccc(F)cn2)CN1]

II followed by contacting the compound of the formula II with a compound of the formula III:

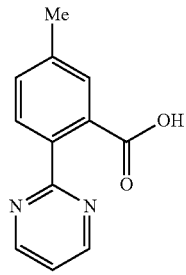

in the presence of a coupling agent, which is selected from the group consisting of: 1-propyl phosphonic anhydride, oxalyl chloride and thionyl chloride;
to give the compound of the formula I, or a pharmaceutically acceptable salt thereof.

6. The process of claim 5 wherein the amino protecting group is a BOC protecting group or a CBZ protecting group.

7. The process of claim 5 wherein the step of contacting the compound of the formula II with the compound of the formula III is conducted in the presence of a weak organic base.

8. The process of claim 7 wherein the weak organic base is diisopropylethylamine or triethylamine.

9. A process for preparing a compound of the formula I:

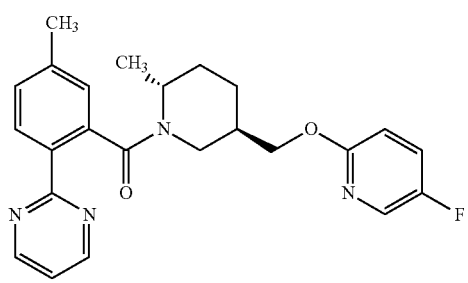

or a pharmaceutically acceptable salt thereof, which comprises:
contacting a camphorsulfonate salt of the formula VII:

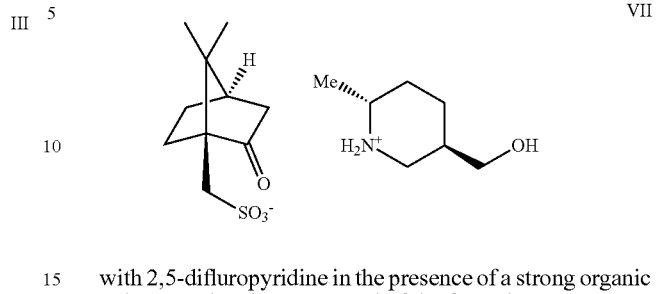

with 2,5-difluropyridine in the presence of a strong organic base to give the compound of the formula II:

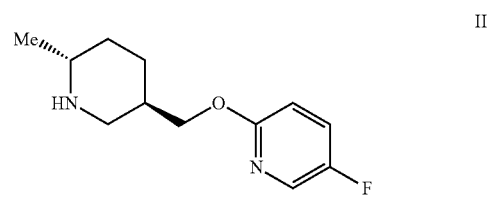 [SMILES: C[C@@H]1CC[C@@H](COc2ccc(F)cn2)CN1]

followed by contacting the compound of the formula II with a compound of the formula III:

III

Me

OH

O

N N in the presence of a coupling agent, which is selected from the group consisting of: 1-propyl phosphonic anhydride, oxalyl chloride and thionyl chloride;
to give the compound of the formula I, or a pharmaceutically acceptable salt thereof.

10. The process of claim 9 wherein the strong organic base is sodium t-butoxide.

* * * * *